(12) United States Patent
Faye et al.

(10) Patent No.: US 6,413,754 B1
(45) Date of Patent: Jul. 2, 2002

(54) KINASE ACTIVATING DEPENDENT CYCLIN PROTEIN KINASES, AND THEIR USES

(75) Inventors: Gérard Faye, Arcueil; Jean-Gabriel Valay, Bernin Cedex; Carl Mann, Magny-les-Hameaux; Jean-Yves Thuret, Orsay, all of (FR)

(73) Assignees: Commissariat a L'Energie Atomique (CEA); Institut Curie; Centre National de la Recherche Scientifique (CNRS), all of Paris (FR)

( * ) Notice: Subject to any disclaimer, the term of this patent is extended or adjusted under 35 U.S.C. 154(b) by 0 days.

(21) Appl. No.: 09/463,962

(22) PCT Filed: Aug. 11, 1998

(86) PCT No.: PCT/FR98/01788

§ 371 (c)(1),
(2), (4) Date: May 26, 2000

(87) PCT Pub. No.: WO99/07836

PCT Pub. Date: Feb. 18, 1999

(30) Foreign Application Priority Data

Aug. 12, 1997 (FR) ............................................. 97 10287

(51) Int. Cl.[7] ............................ C12N 9/12; C12N 1/14; C12N 1/16; C12P 21/06; A01N 37/18

(52) U.S. Cl. ...................... 435/194; 435/183; 435/69.1; 435/252.3; 435/254.1; 435/254.2; 435/254.22; 514/2

(58) Field of Search ................................. 435/183, 194, 435/243, 254.1, 254.2, 254.22; 424/9.34; 514/2

(56) References Cited

FOREIGN PATENT DOCUMENTS

WO          WO 97 16447 A          5/1997

OTHER PUBLICATIONS

Thuret J.Y. et al.: "Civl (CAK in vivo), a novel Cdk–activating kinase" Cell, vol. 86, No. 4, Aug. 23, 1996, pp. 565–576, XP002065325 in the application see the whole document.

*Primary Examiner*—Ponnathapu Achutamurthy
*Assistant Examiner*—Manjunath N. Rao
(74) *Attorney, Agent, or Firm*—Oblon, Spivak, McClelland, Maier & Neustadt, P.C.

(57) ABSTRACT

The invention concerns the family of protein-kinases having the following common characteristics: they are devoid of the consensus pattern GxGx(Y/F)GxV; they have a dependent non-cyclin CAK activity. The inhibitors of the protein-kinases of this family can be used as fungicides.

17 Claims, 1 Drawing Sheet

KINASE ACTIVATING DEPENDENT CYCLIN PROTEIN KINASES, AND THEIR USES

Figure 1:
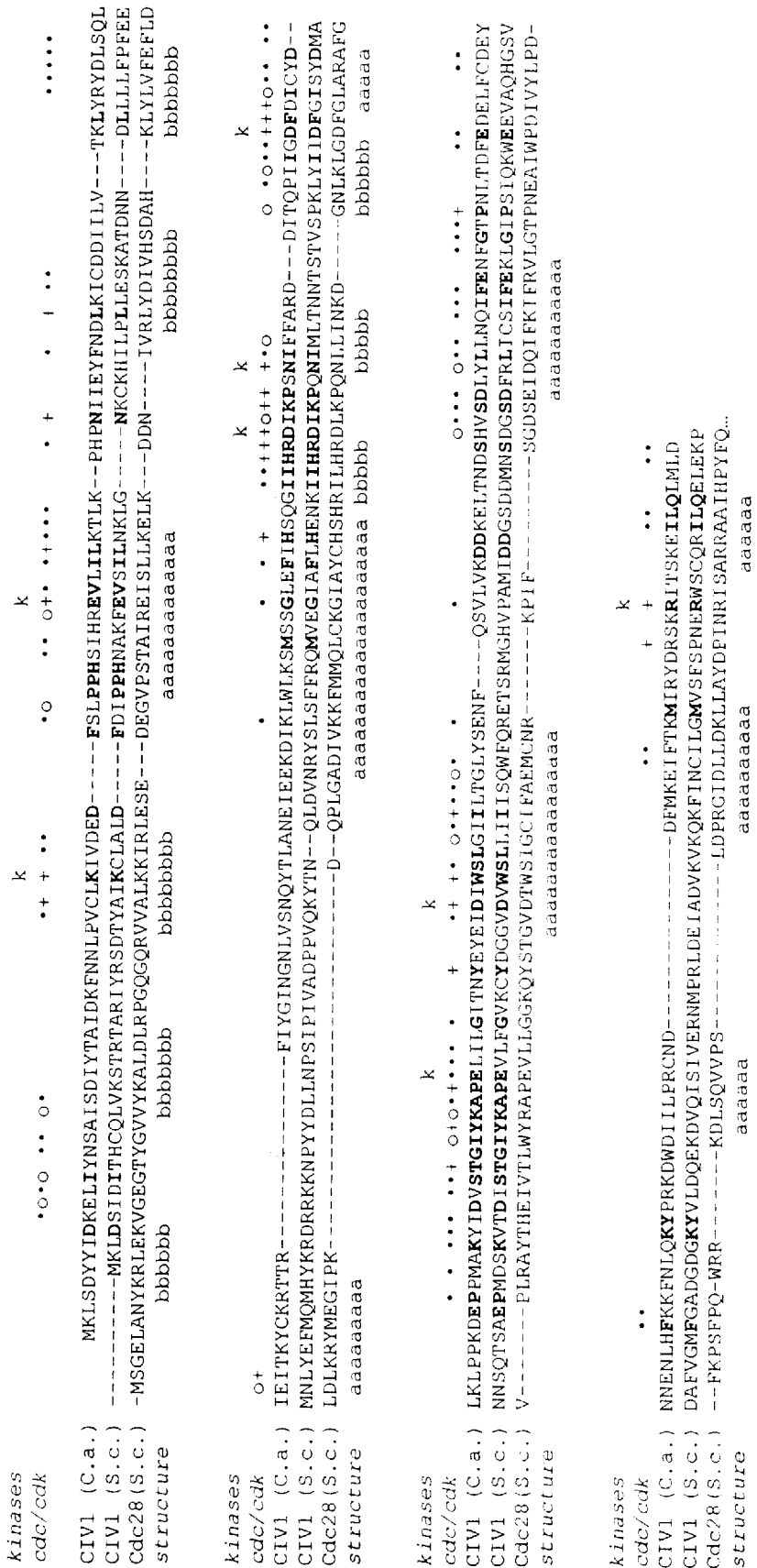

The present invention relates to a new cycline-dependent protein kinase-activating kinase from *Candida albicans* and to its uses.

Cycline-dependent protein kinases (Cdk) are cell division cycle regulators in eukaryotes which are essential both at the level of the G1/S transition and the G2/M transition of the cell cycle. The CDC28 of *Saccharomyces cerevisae* and the CDC2 of *Schizosaccharomyces pombe* are the first Cdks which have been identified.

The activation of the Cdks requires both the attachment of a molecule of cycline, and the phosphorylation of the Cdk on a conserved threonine residue situated in a region called: "T loop".

It has been shown that this phosphorylation is carried out by a kinase called: "Cdk-activating kinase" (CAK), which, in vertebrates, exists in the form of a heterotrimer comprising a catalytic subunit called Cdk7, a subunit of the cycline type, called cycline H, and a factor MAT-1 [for a review, cf. SOLOMON, Trends Biochem. Sci. 19, 496–500 (1994)]. The Cdk7-cycline H complex is in addition a component of the TFIIH complex, which is necessary for the basal transcription of genes by RNA polymerase II, and is involved in the phosphorylation of the repeat sequences of the carboxy-terminal domain (CTD) of the large subunit of this polymerase.

In the fission yeast *Schizosaccharomyces pombe*, a complex similar to Cdk7-cycline H, comprising a catalytic subunit called Crk1, and a regulatory cycline called Mcs2, has been identified. It has been shown that the Crk1 gene was essential for cell viability, and it has been observed in vitro that the complex Crk1-Mcs2 was associated with the CAK activity and with the CTD-kinase activity [BUCK et al., EMBO J., 14(24), 6173–83 (1995); DAMAGNEZ et al., EMBO J., 14(24), 6164–72, (1995)].

In the budding yeast *Saccharomyces cerevisiae*, a complex comprising a kinase (Kin28) and a cycline (Ccl1) respectively related, at the level of their sequence, to the kinases Cdk7 and Crk1, and to the regulatory proteins cycline H and Mcs2, has also been identified. The complex Kin28-Ccl1 forms part of the complex TFIIH and has a CTD-kinase activity, but is not involved in the CAK activity.

Recently, the inventors have identified a kinase responsible for the CAK activity in *Saccharomyces cerevisiae*. This kinase was called CIV1 (CAK in vivo), and the corresponding gene was called CIV1 (THURET et al., Cell, 86(4), 1996). These results have been confirmed by other teams [KALDIS et al., Cell, 86(4), 553–564 (1996); ESPINOZA et al., Science, 273(5282), 1714–1717 (1996)]. The *Saccharomyces cerevisiae* CAK is overall related to the serine-threonine-kinase family, and in particular to the protein kinases CDC2 and CDC28, and differs from the CAKs previously identified in other organisms by the absence of the glycine-rich conserved motif GxGx(Y/F)GxV, which is present in most protein kinases, the presence of inserts of 5 to 29 amino acids, which are situated between the components of secondary structure which are conserved in the Cdk family, and by the fact that its CAK activity does not require its incorporation into an enzymatic complex.

The CAK activity of CIV1 being essential for cellular division and survival, the inventors have undertaken to investigate if there are, in pathogenic yeasts, genes homologous to CIV1, encoding protein kinases possessing a CAK activity. Indeed, in this case, the obtaining of means of regulating this activity, and in particular of inhibitors, would be of great interest from an industrial or therapeutic point of view, mainly for the production of fungicides.

With this aim in view, the inventors first undertook the screening of DNA libraries from the pathogenic yeast *Candida albicans* using probes derived from various regions of the *Saccharomyces cerevisiae* CIV1 gene. However, none of the probes used have made it possible to detect the presence of homologous sequences in the *Candida albicans* genome.

The inventors have, however, investigated whether *Candida albicans* possibly possesses a functional analogue of the *Saccharomyces cerevisiae* CAK by examining if there are in *Candida albicans* one or more genes capable of restoring in *Saccharomyces cerevisiae* the CAK function in a heat-sensitive mutant of the CIV1 gene. They thus succeeded in identifying a *Candida albicans* gene capable of complementing on its own the deficient CAK function in the mutant.

The sequence of this gene, called CaCIV1, has been determined; it is represented in the sequence listing in the annex under the number SEQ ID NO:1; the sequence of its translational product, called CaCIV1, is represented under the number SEQ ID NO:2.

FIG. 1 represents the comparison of the amino acid sequence (1-letter code) of CaCIV1 (SEQ ID NO:1) with that of the *Saccharomyces cerevisiae* CAK (called ScCIV1), and with that of the *Saccharomyces cerevisiae* kinase CDC28 (called ScCDC28). The residues conserved in ScCIV1 and CaCIV1 are in bold characters.

Legend to the annotations of FIG. 1:

k=residue conserved in most protein kinases;

●=residue often present in the Cdk family;

○=residue always present in the Cdk family;

+=residue present in the Cdk family and in ScCIV1;

secondary structures: a=α helix; b=β sheet.

CaCIV1 only exhibits at the level of the overall amino acid sequence a 28% identity with the CAK of *Saccharomyces cerevisiae*, ScCIV1.

However, the similarities observed between ScCIV1 and CaCIV1 make it possible to define a kinase family, called hereinafter CIV1, grouping together proteins having the following characteristics:

they lack the motif GxGx(Y/F)GxV, in which G represents glycine, x represents any amino acid, Y/F represents either tyrosine or phenylalanine, V represents valine;

they possess a non-cycline-dependent CAK activity.

The present invention encompasses the protein kinases belonging to the CIV1 family as defined above, with the exception of the *Saccharomyces cerevisiae* CAK ScCIV1.

According to a preferred embodiment of the present invention, the said protein kinase is capable of being obtained from an ascomycete, advantageously a hemiascomycete, and preferably *Candida albicans*.

A protein kinase in accordance with the invention is for example represented in the sequence listing in the annex under the number SEQ ID NO:2.

The subject of the present invention is also a nucleic acid sequence encoding a protein kinase in accordance with the invention.

A nucleic acid sequence in accordance with the invention consists for example of the sequence SEQ ID NO:1 of the sequence listing in the annex.

The subject of the present invention is also nucleic acid fragments of at least 18 bp, homologous or complementary to a nucleic acid sequence encoding a peptide sequence specific to the CAK in accordance with the invention.

These fragments may in particular be used as hybridization probes, and/or amplification primers, to isolate and/or to clone using *Candida albicans*, a nucleic acid sequence encoding a CAK in accordance with the invention.

The present invention also encompasses nucleic acid fragments of at least 15 bp, preferably of at least 18 bp, homologous or complementary to a nucleic acid sequence encoding a peptide sequence conserved in the protein kinase family defined by the CAK CaCIV1 in accordance with the invention, and the *Saccharomyces cerevisiae* CAK ScCIV1.

These fragments may in particular be used as hybridization probes, and/or amplification primers, to detect the existence, in organisms other than *Saccharomyces cerevisiae* and *Candida albicans*, of sequences encoding kinases related to CAK CaCIV1 and ScCIV1 and to isolate and/or to clone the genes thus identified. The invention also encompasses the nucleic acid sequences obtained in this manner, and the protein kinases of the CAK CaCIV1 and ScCIV1 family which are encoded by these sequences.

The subject of the present invention is also any recombinant vector, and in particular any expression vector, resulting from the insertion of at least one nucleic acid sequence in accordance with the invention into an appropriate vector. The choice of an appropriate vector can be easily made by persons skilled in the art, among numerous available vectors, depending on the host cell chosen to multiply and/or to express a nucleic acid in accordance with the invention.

The invention also encompasses prokaryotic or eukaryotic cells transformed with a nucleic acid sequence in accordance with the invention. These transformed cells can be used in particular to express a kinase in accordance with the invention, for example so as to purify it from cell cultures, for example using techniques similar to those previously described by the inventors for *Saccharomyces cerevisiae* CIV1 (THURET et al., 1996, publication cited above), or alternatively so as to detect its activity by an appropriate test of cell viability.

The demonstration, by the inventors, of the functional homology of the kinases ScCIV1 and CaCIV1 makes it possible to envisage numerous applications for this kinase family.

In particular, because it appears that the non-cycline-dependent CAK activity of this kinase family is essential for cell division and survival, substances inhibiting this activity may be used as fungicides, either as medicaments or on an industrial level.

For example, to screen fungicidal substances such as substances which are active on *Candida albicans*, the kinase activity of CaCIV1, or of one of its functional homologues consisting of a non-cycline-dependent CAK of the CIV1 family, is measured in the presence of each of the products for which it is desired to determine the fungicidal properties, and the products having an inhibitory effect on this activity are selected.

Such a screening can be carried out by measuring the kinase activity of a CAK of the CIV1 family, in the presence of potential activators or inhibitors to be tested. The kinase activity may, for example, be measured in vitro, either directly by detecting the phosphorylation of a peptide or of a substrate protein, for example CDC28 or Cdk2, or the protein MBP (myelin basic protein), in an appropriate reaction mixture, or indirectly, by detecting and/or measuring the activity of the substrate protein when the latter depends on phosphorylation.

The kinase activity can also be measured in vivo, by a test of cell viability; for example, the kinase activity of CaCIV1 can be advantageously measured in cells of a mutant of *Saccharomyces cerevisiae* not expressing CAK ScCIV1, which are transformed with the CaCIV1 gene.

The invention also encompasses the use of a product selected as indicated above for its inhibitory properties of a non-cycline-dependent CAK of the CIV1 family for the production of a fungicide.

The present invention will be understood more clearly with the aid of the additional description which follows, which refers to an example illustrating the detection of the CAK activity of CaCIV1, and the cloning of the corresponding gene.

EXAMPLE

The *Saccharomyces cerevisiae* strain, CMY975 (genotype CIV1–2 ura3 leu2 trp1 lys2 ade2 ade3) carries a heat-sensitive mutation of the CIV1 gene and, because of this, grows at 24° C., but not at 37° C.

A culture of this strain was transformed by the lithium acetate method [SCHIESTL and GIETZ, Current Genetics, 16, 339–346, (1989)] with a library of *Candida albicans* Sau3A genomic fragments cloned into the BamHI site of the vector YEp24 (multicopy-URA3) [Botstein et al., Gene 8, 17–24, (1979)].

The CMY975 cells are plated on dishes containing a uracil-free synthetic medium, and cultured at 37° C.

Ten colonies of CMY975 growing under these conditions were obtained. These plasmids YEp24 containing *Candida albicans* inserts were recovered from each of these colonies, and amplified in *Escherichia coli*.

The restriction map of each of these plasmids was established, and made it possible to observe that all the inserts came from the same region of the *Candida albicans* genome. Sequencing of this region made it possible to identify the same open reading frame encoding a protein kinase of 339 amino acids, which shows that the 10 inserts separately obtained correspond to one and the same *Candida albicans* gene. This gene was called CaCIV1.

The sequence of CaCIV1 is represented in the sequence listing in the annex under the number SEQ ID NO:1, and that of the protein CaCIV1 is represented under the number SEQ ID NO:2. Comparison of the sequence of the protein CaCIV1 with the sequences available in data bases reveals that this protein has only 28% of amino acids identical with the CAK of *Saccharomyces cerevisiae* ScCIV1, and 24% of amino acids identical with the Cdk ScCDC28 of *Saccharomyces cerevisiae* and the CaCDC28 of *Candida albicans*.

A BamHI-ClaI genomic fragment of 3 kb containing the CaCIV1 gene was subcloned into the centromeric plasmid TRP1 pRS414 [SIKORSKI and HIETER, Genetics, 122, 19–27 (1989)]. This plasmid was used to transform a *Saccharomyces cerevisiae* mutant in which the ScCIV1 sequence is deleted from the genome and containing the ScCIV1 gene on a replicative plasmid also carrying the selectable gene URA3 (strain CMY116 of the genome ura3 leu2 trp1 lys2 civ1 LEU2/pJG43 (URA3-ScCIV1)). The cells transformed with the plasmid pRS414-CaCIV1 are viable after counterselection and the loss of the plasmid pJG43 (URA3-ScCIV1), which confirms that the CaCIV1 gene can function in place of the essential ScCIV1 gene. Therefore, CaCIV1 encodes a functional homologue of ScCIV1, and is sufficient to restore the CAK activity.

What is claimed is:

1. An isolated *Candida albicans* protein kinase (CIV1), which lacks the motif GxGx (Y/F)GxV;
   wherein G is Glycine, x is any amino acid, Y/F is tyrosine or phenylalanine and v is valine;
   wherein said isolated protein kinase has non-cyclin dependent cdk-activating activity; and
   wherein said isolated protein kinase is not a *Saccharomuces cerivisiae* CIV1.

2. The isolated protein kinase of claim 1, which comprises the amino acid sequence of SEQ ID NO:2.

3. An isolated polynucleotide which encodes the isolated protein kinase of claim 1.

4. The isolated polynucleotide of claim 3, which comprises the nucleotide sequence of SEQ ID NO:1.

5. A vector comprising the isolated polynucleotide of claim 3.

6. A eukaryotic or prokaryotic cell comprising the polynucleotide of claim 3.

7. A method of screening for polynucleotides which encode a protein having non-cyclin dependent cdk-activating activity comprising hybridizing the isolated polynucleotide of claim 4 to the polynucleotide to be screened; expressing the hybridized polynucleotide to produce a protein; and detecting the presence or absence of non-cyclin dependent cdk-activating activity in said protein.

8. A method of screening for polynucleotides which encode a protein having non-cyclin dependent cdk-activating activity comprising hybridizing a polynucleotide fragment of SEQ ID NO:1 to the polynucleotide to be screened, wherein said polynucleotide fragment is at least 15 basepairs; expressing the hybridized polynucleotide to produce a protein; and detecting the presence or absence of non-cyclin dependent cdk-activating activity in said protein.

9. A method of producing a non-cyclin dependent cdk-activating protein kinase comprising culturing the cell of claim 6; and collecting the non-cyclin dependent cdk-activating kinase produced.

10. A method of screening for substances which inhibit the activity of the isolated kinase of claim 1, comprising contacting the isolated kinase with the substance to be detected and measuring the non-cyclin dependent cdk-activating activity in said contacted isolated kinase.

11. The method of claim 10, wherein said substances are fungicidal substances.

12. A method of producing a fungicide, comprising:
   identifying a fungicidal product according to the method of claim 11, and then formulating the fungicidal product into a fungicide.

13. A method of screening for substances which inhibit the activity of the isolated kinase of claim 1, comprising contacting a cell which expresses the isolated kinase with the substance to be detected and measuring the non-cyclin dependent cdk-activating activity in said contacted cell expressing the isolated kinase.

14. The method of claim 13, wherein the substances are fungicidal substances.

15. The method of claim 13, wherein the cell is a fungal cell.

16. The method of claim 13, wherein the cell is a *Candida albicans* cell.

17. A method of producing a fungicide, comprising:
   identifying a fungicidal product according to the method of claim 14, and then formulating the fungicidal product into a fungicide.

* * * * *

SEQUENCE LISTING

<160> NUMBER OF SEQ ID NOS: 2

<210> SEQ ID NO 1
<211> LENGTH: 1020
<212> TYPE: DNA
<213> ORGANISM: Candida albicans
<220> FEATURE:
<221> NAME/KEY: CDS
<222> LOCATION: (1)..(1020)

<400> SEQUENCE: 1

| | | | | | | | | | | | | | | | | |
|---|---|---|---|---|---|---|---|---|---|---|---|---|---|---|---|---|
| atg | aag | ttg | tca | gat | tat | tat | ata | gac | aag | g aa | tta | att | tac | aat | agt | 48 |
| Met | Lys | Leu | Ser | Asp | Tyr | Tyr | Ile | Asp | Lys | G lu | Leu | Ile | Tyr | Asn | Ser | |
| 1 | | | | 5 | | | | | 10 | | | | | 15 | | |
| gcc | att | tct | gat | ata | tat | agc | gct | att | gat | a ag | ttt | aat | aac | tta | cca | 96 |
| Ala | Ile | Ser | Asp | Ile | Tyr | Ser | Ala | Ile | Asp | L ys | Phe | Asn | Asn | Leu | Pro | |
| | | | | 20 | | | | | 25 | | | | | 30 | | |
| gta | tgt | ctt | aaa | ata | gtt | gat | gaa | gat | ttc | a gt | ctt | cca | cca | cat | tca | 144 |
| Val | Cys | Leu | Lys | Ile | Val | Asp | Glu | Asp | Phe | S er | Leu | Pro | Pro | His | Ser | |
| | | 35 | | | | | 40 | | | | | 45 | | | | |
| atc | cat | cga | gaa | gtt | ctt | ata | ctt | aaa | act | t tg | aaa | cca | cat | cca | aac | 192 |
| Ile | His | Arg | Glu | Val | Leu | Ile | Leu | Lys | Thr | L eu | Lys | Pro | His | Pro | Asn | |
| | 50 | | | | | 55 | | | | | 60 | | | | | |
| ata | att | gaa | tat | ttt | aat | gat | ctt | aaa | att | t gt | gac | gat | att | ata | tta | 240 |
| Ile | Ile | Glu | Tyr | Phe | Asn | Asp | Leu | Lys | Ile | C ys | Asp | Asp | Ile | Ile | Leu | |
| 65 | | | | | 70 | | | | | 75 | | | | | 80 | |
| gtc | acc | aaa | ttg | tat | cgt | tat | gat | ttg | agt | c aa | ttg | att | gaa | att | aca | 288 |
| Val | Thr | Lys | Leu | Tyr | Arg | Tyr | Asp | Leu | Ser | G ln | Leu | Ile | Glu | Ile | Thr | |
| | | | | 85 | | | | | 90 | | | | | 95 | | |
| aaa | tat | tgt | aaa | cga | aca | aca | cga | ttt | att | t at | ggt | att | aat | ggt | aat | 336 |
| Lys | Tyr | Cys | Lys | Arg | Thr | Thr | Arg | Phe | Ile | T yr | Gly | Ile | Asn | Gly | Asn | |
| | | | | 100 | | | | | 105 | | | | | 110 | | |
| ctt | gtt | agt | aat | caa | tat | aca | ctt | gct | aat | g aa | att | gaa | gaa | aaa | gat | 384 |
| Leu | Val | Ser | Asn | Gln | Tyr | Thr | Leu | Ala | Asn | G lu | Ile | Glu | Glu | Lys | Asp | |
| | | | 115 | | | | | 120 | | | | | 125 | | | |
| atc | aaa | tta | tgg | tta | aaa | tca | atg | agt | tca | g ga | ctt | gaa | ttt | att | cat | 432 |
| Ile | Lys | Leu | Trp | Leu | Lys | Ser | Met | Ser | Ser | G ly | Leu | Glu | Phe | Ile | His | |
| | | 130 | | | | | 135 | | | | | 140 | | | | |
| tca | caa | ggg | ata | att | cat | cgt | gat | ata | aaa | c cc | agt | aat | att | ttc | ttt | 480 |
| Ser | Gln | Gly | Ile | Ile | His | Arg | Asp | Ile | Lys | P ro | Ser | Asn | Ile | Phe | Phe | |
| 145 | | | | | 150 | | | | | 155 | | | | | 160 | |
| gcc | cgg | gat | gat | ata | aca | caa | ccg | att | att | g ga | gat | ttt | gat | att | tgt | 528 |
| Ala | Arg | Asp | Asp | Ile | Thr | Gln | Pro | Ile | Ile | G ly | Asp | Phe | Asp | Ile | Cys | |
| | | | | 165 | | | | | 170 | | | | | 175 | | |
| tat | gat | tta | aaa | ctg | cca | cct | aaa | gat | gaa | c cc | cct | atg | gcg | aaa | tat | 576 |
| Tyr | Asp | Leu | Lys | Leu | Pro | Pro | Lys | Asp | Glu | P ro | Pro | Met | Ala | Lys | Tyr | |
| | | | | 180 | | | | | 185 | | | | | 190 | | |
| att | gat | gta | tct | aca | ggt | att | tat | aaa | gca | c ca | gaa | ttg | att | ctt | ggt | 624 |
| Ile | Asp | Val | Ser | Thr | Gly | Ile | Tyr | Lys | Ala | P ro | Glu | Leu | Ile | Leu | Gly | |
| | | | 195 | | | | | 200 | | | | | 205 | | | |
| ata | act | aat | tat | gaa | tat | gaa | att | gat | att | t gg | tca | ttg | ggt | ata | att | 672 |
| Ile | Thr | Asn | Tyr | Glu | Tyr | Glu | Ile | Asp | Ile | T rp | Ser | Leu | Gly | Ile | Ile | |
| | | 210 | | | | | 215 | | | | | 220 | | | | |
| ttg | act | ggt | tta | tat | tca | gaa | aat | ttt | caa | a gt | gtt | tta | gtc | aaa | gat | 720 |
| Leu | Thr | Gly | Leu | Tyr | Ser | Glu | Asn | Phe | Gln | S er | Val | Leu | Val | Lys | Asp | |
| 225 | | | | | 230 | | | | | 235 | | | | | 240 | |
| gat | aaa | gaa | ttg | act | aat | gat | tct | cat | gtt | a gt | gat | tta | tat | tta | tta | 768 |
| Asp | Lys | Glu | Leu | Thr | Asn | Asp | Ser | His | Val | S er | Asp | Leu | Tyr | Leu | Leu | |
| | | | | 245 | | | | | 250 | | | | | 255 | | |

```
                                                                                    -continued aat caa ata ttt gaa aat ttc ggt aca ccc a at tta act gat ttt gaa                    816
Asn Gln Ile Phe Glu Asn Phe Gly Thr Pro A sn Leu Thr Asp Phe Glu
            260                 265                 270 gat gaa tta ttt tgt gat gaa tat aat aat g aa aac ttg cat ttt aaa                    864
Asp Glu Leu Phe Cys Asp Glu Tyr Asn Asn G lu Asn Leu His Phe Lys
            275                 280                 285 aaa ttc aat tta caa aaa tat cct aga aaa g at tgg gat att att tta                    912
Lys Phe Asn Leu Gln Lys Tyr Pro Arg Lys A sp Trp Asp Ile Ile Leu
            290                 295                 300 cct cga tgc aat gat gat ttc atg aaa gaa a tt ttt acc aag atg att                    960
Pro Arg Cys Asn Asp Asp Phe Met Lys Glu I le Phe Thr Lys Met Ile
305                 310                 315                 320 aga tat gat cga agt aaa aga ata act tct a aa gaa atc tta caa tta                   1008
Arg Tyr Asp Arg Ser Lys Arg Ile Thr Ser L ys Glu Ile Leu Gln Leu
                325                 330                 335 atg tta gat tga                                                                    1020
Met Leu Asp <210> SEQ ID NO 2
<211> LENGTH: 339
<212> TYPE: PRT
<213> ORGANISM: Candida albicans

<400> SEQUENCE: 2

Met Lys Leu Ser Asp Tyr Tyr Ile Asp Lys G lu Leu Ile Tyr Asn Ser
1               5                   10                  15

Ala Ile Ser Asp Ile Tyr Ser Ala Ile Asp L ys Phe Asn Asn Leu Pro
            20                  25                  30

Val Cys Leu Lys Ile Val Asp Glu Asp Phe S er Leu Pro Pro His Ser
        35                  40                  45

Ile His Arg Glu Val Leu Ile Leu Lys Thr L eu Lys Pro His Pro Asn
    50                  55                  60

Ile Ile Glu Tyr Phe Asn Asp Leu Lys Ile C ys Asp Ile Ile Leu
65                  70                  75                  80

Val Thr Lys Leu Tyr Arg Tyr Asp Leu Ser G ln Leu Ile Glu Ile Thr
                85                  90                  95

Lys Tyr Cys Lys Arg Thr Thr Arg Phe Ile T yr Gly Ile Asn Gly Asn
            100                 105                 110

Leu Val Ser Asn Gln Tyr Thr Leu Ala Asn G lu Ile Glu Glu Lys Asp
        115                 120                 125

Ile Lys Leu Trp Leu Lys Ser Met Ser Ser G ly Leu Glu Phe Ile His
    130                 135                 140

Ser Gln Gly Ile Ile His Arg Asp Ile Lys P ro Ser Asn Ile Phe Phe
145                 150                 155                 160

Ala Arg Asp Asp Ile Thr Gln Pro Ile Ile G ly Asp Phe Asp Ile Cys
                165                 170                 175

Tyr Asp Leu Lys Leu Pro Pro Lys Asp Glu P ro Pro Met Ala Lys Tyr
            180                 185                 190

Ile Asp Val Ser Thr Gly Ile Tyr Lys Ala P ro Glu Leu Ile Leu Gly
        195                 200                 205

Ile Thr Asn Tyr Glu Tyr Glu Ile Asp Ile T rp Ser Leu Gly Ile Ile
    210                 215                 220

Leu Thr Gly Leu Tyr Ser Glu Asn Phe Gln S er Val Leu Val Lys Asp
225                 230                 235                 240

Asp Lys Glu Leu Thr Asn Asp Ser His Val S er Asp Leu Tyr Leu Leu
                245                 250                 255
```

```
                                    -continued

Asn Gln Ile Phe Glu Asn Phe Gly Thr Pro A sn Leu Thr Asp Phe Glu
            260             265             270

Asp Glu Leu Phe Cys Asp Glu Tyr Asn Asn G lu Asn Leu His Phe Lys
            275             280             285

Lys Phe Asn Leu Gln Lys Tyr Pro Arg Lys A sp Trp Asp Ile Ile Leu
    290             295             300

Pro Arg Cys Asn Asp Asp Phe Met Lys Glu I le Phe Thr Lys Met Ile
305             310             315             320

Arg Tyr Asp Arg Ser Lys Arg Ile Thr Ser L ys Glu Ile Leu Gln Leu
            325             330             335

Met Leu Asp
```